United States Patent [19]

Ishii et al.

[11] Patent Number: 5,268,484

[45] Date of Patent: Dec. 7, 1993

[54] 5-SUBSTITUTED 2-OXAZOLIDINONES

[75] Inventors: Toshiyuki Ishii, Sakai; Mitsuo Yamada, Suita, both of Japan

[73] Assignee: Nippon Paint Co., Ltd., Osaka, Japan

[21] Appl. No.: 941,295

[22] Filed: Sep. 4, 1992

[30] Foreign Application Priority Data

Sep. 5, 1991 [JP] Japan ................ 3-254417

[51] Int. Cl.$^5$ .................. C07D 263/24
[52] U.S. Cl. ..................... 548/232
[58] Field of Search .................. 548/232

[56] References Cited

U.S. PATENT DOCUMENTS

| | | | |
|---|---|---|---|
| 3,654,298 | 4/1972 | Douzon et al. | 548/232 |
| 4,287,351 | 9/1981 | Bourgery et al. | 548/232 |
| 5,182,296 | 1/1993 | Nakai | 514/376 |

FOREIGN PATENT DOCUMENTS

| | | | |
|---|---|---|---|
| 0425209 | 5/1991 | European Pat. Off. | 548/232 |
| 479436 | 4/1992 | European Pat. Off. | |

OTHER PUBLICATIONS

Nakai et al. Chem. Abstr vol. 115(7) Entry 71581u(1991) abstracting EP 425209

*Primary Examiner*—Donald G. Daus
*Attorney, Agent, or Firm*—Millen, White, Zelano, & Branigan

[57] ABSTRACT

5-alkoxymethyl or alkenyloxymethyl-2-oxazolidines, particularly those having a long chain alkyl or alkenyl moiety are useful as a internal mold release in the polyurea reaction injection molding technology.

10 Claims, No Drawings

5-SUBSTITUTED 2-OXAZOLIDINONES

BACKGROUND OF THE INVENTION

This invention relates to a novel 2-oxazolidinone derivatives having an etherfied methyl group on the 5th position.

A number of 5-aryloxymethyl-2-oxazolidinone compounds are known in the literature. For examples, 5-[(2methoxyphenoxy)methyl]-2-oxazolidinone is an anxiolytic and muscle relaxant agent known by the generic name mephenoxlone. To our best knowledge, corresponding 5-alkoxymethyl or alkenyloxymethyl-2-oxazolidinones, particularly those having a long chain aliphatic hydrocarbon group as well as their pharmacological activities are not known.

SUMMARY OF THE INVENTION

We have now discovered that 5-alkoxymethyl or alkenyloxymethyl-2-oxazolinones, particularly those having a long chain aliphatic moiety are useful as an internal mold release in the polyurea reaction injection molding (RIM) technology.

The compounds of this invention has the formula I:

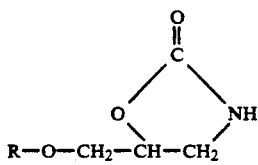

wherein R is an aliphatic hydrocarbon group having up to 20 carbon atoms.

DETAILED DESCRIPTION OF THE INVENTION

The compounds of formula (I) may be synthesized, by a cyclization reaction which is well-known in the organic chemistry, viz. by reacting a glycidyl ether of the formula II:

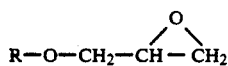

wherein R is as defined, with a carbamate ester of the formula III:

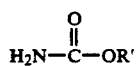

wherein R' is an ester residue.

Examples of glycidyl ethers of the formula II include methyl glycidyl ether, allyl glycidyl ether, isopropyl glycidyl ether, n-butyl glycidyl ether, 2-ethylhexyl glycidyl ether, octyl glycidyl ether, decyl glycidyl ether, lauryl glycidyl ether, myristyl glycidyl ether, palmityl glycidyl ether, stearyl glycidyl ether, oleyl glycidyl ether, 2-methyloctyl glycidyl ether and the like. $C_8$–$C_{20}$ alkyl or alkenyl ethers are preferable including their mixtures derived from naturally occurring oil and fats.

The ester residue R' of the carbamate of the formula III is a leaving group and, therefore, may be any hydrocarbon moiety including $C_1$–$C_{10}$ aliphatic hydrocarbon radicals, aromatic or arylaliphatic hydrocarbon radicals which may optionally have a substituent such as hydroxyl. Specific examples thereof include methyl, ethyl, isopropyl, butyl, benzyl, phenyl, 2-hydroxyethyl and so on. Methyl, ethyl or 2-hydroxyethyl ester is easily available and thus preferable.

The reaction may be carried out by heating both reactants without solvent while expelling an alcohol corresponding to the ester residue R' from the reaction mixture by, for instance, blowing nitrogen gas into the reaction mixture. It is known that the above reaction may be promoted by adding thereto a small amount of a tertiary amine as a catalyst. We have discovered that when using a tertiary amine and a tin compound as a catalyst in the above reaction in combination, the desired oxazolidinone compound may be obtained in an unexpectedly good yield. Examples of usable tertiary amines include aliphatic amines such as triethylamine or N, N, N', N'-tetramethylethylenedi amine; alicyclic amines such as N, N-dimethylcyclohexylamine aralkylamines such as N, N-dimethylbenzylamine; aromatic amines such as N, N-dimethylaniline; and heterocyclic amines such as pyridine, quinoline, imidazole, N-methylmorpholine, 1, 4-diazabicyclo [2.2.2.]octane or 1, 8-diazabicyclo [5.4.0]-7-undecene. Examples of usable tin compounds include stannous chloride, dibutyltin dilaurate, stannous octenate, dibutyltin oxide, dioctyltin oxide, 1, 3-diacetoxytetrabutyldistannoxane, 1, 3-dichlorotetrabutylstan noxane, dibutyldibutoxytin and so on.

The compounds the formula (I), particularly those having a long chain alkyl or alkenyl moiety may be incorporated into a polyurea RIM composition as an internal mold release whereupon the compound is eventually immobilized to the molding by the reaction with the polyamine component thereof to form a urea linkage.

The following examples are for illustrative purposes only without limiting the invention thereto.

EXAMPLE 1

8.9 g (0.10 mole) of ethyl carbamate was dissolved in 13.0g (0.10 mole) of n-butyl glycidyl ether. After adding 0.2g of N, N-dimethylbenzylamine and 0.2g of di-n-butyltin dilaurate, the solution was heated at 160° C. for 2 hours while blowing nitrogen gas into the reaction mixture to remove ethanol. The product was distilled under reduced pressure to give 16.2 g (94% of theory) of 5-n-butoxymethyl-2-oxazolidinone boiling at 203–205° C./3 mmHg, $^1$H-NMR (DMSO, δ) ; 0.71–1.00 (t, 3H), 1.10–1.62 (m,4H), 3.05–3.61 (m,6H), 4.53–4.80 (m,1H), 7.53 (bs, 1H).

EXAMPLE 2

35.6g (0.40 mole) of ethyl carbamate was dissolved in 45.6g (0.40 mole) of allyl glycidyl ether. After adding 1.6 g of N, N-dimethylbenzylamine and 2.5 g of di-n-butyltin dilaurate, the solution was heated at 150° C. for 1 hour while blowing nitrogen gas into the reaction mixture to remove ethanol. The product was distilled under reduced pressure to give 61.7 g (98% of theory) of 5-allyloxymethyl-2-oxazolidinone boiling at 203–205° C./3

$^1$H-NMR (CDCl$_3$, δ); 3.31–3.55 (dd, 1H), 3.61(d, 2H), 3.65(dd, 1H), 4.06(d, 2H), 4.60–5.00 (m, 1H), 5.10–5.40 (m, 2H), 5.69–6.17 (m, 1H), 6.75 (bs, 1H).

EXAMPLE 3

8.9 g (0.10 mole) of ethyl carbamate was dissolved in 18.6 g (0.10 mole) of 2-ethylhexyl glycidyl ether. After adding 0.41 g of N, N-dimethylbenzylamine and 0 63 g of di-n-butyltin dilaurate, the solution was heated at 160° C. for 1 hour while blowing nitrogen gas into the reaction mixture. The product was distilled under reduced pressure to give 20.0 g (88% of theory) of 5-(2-ethylhexyl) oxymethyl-2-oxazolidinone.

$^1$H-NMR (CDCl$_3$, δ) ; 0.70–1.00 (m, 6H), 1.10–1.70(m, 7H), 3.31–3.51(m, 3H), 3.51–3.78(m, 3H), 4.60–4.90 (m, 1H), 6.53(bs, 1H)

EXAMPLE 4

4.45 g (0.050 mole) of ethyl carbamate was dissolved in 16.3 g (0.050 mole) of stearyl glycidyl ether. After adding 2.0 g of N, N-dimethylbenzylamine and 2.0 g of di-n-butyltin dilaurate, the solution was heated at 160° C. for 1 hour while blowing nitrogen gas into the reaction mixture. The product was purified by silica gel column chromatography (developing solvent, hexane: ethyl acetate=4:1) to give 15.9 g (85% of theory) of 5-stearyloxymethyl-2- oxazolidinone.

$^1$H-NMR (CDCl$_3$, δ); 0.70–1.00 (m, 3H), 1.10–1.70 (m, 32H), 3.31–3.51 (m, 3H), 3.51–3.78 (m, 3H), 4.60–4.90 (m, 1H), 6.53 (bs, 1H)

What is claimed is:

1. A compound of the formula:

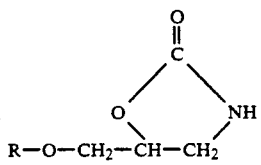

wherein R is a fatty aliphatic hydrocarbon group having 8 to 20 carbon atoms.

2. The compound according to claim 1, wherein said aliphatic hydrocarbon group has from 8 to 20 carbon atoms.

3. The compound according to claim 2, wherein said aliphatic hydrocarbon group is an alkyl.

4. The compound according to claim 2, wherein said aliphatic hydrocarbon group is an alkenyl.

5. A method for preparing the compound of claim 1 which comprises:

reacting a glycidyl ether of the formula:

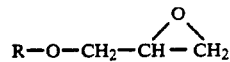

wherein R is a fatty aliphatic hydrocarbon group having 8 to 20 carbon atoms, with a carbamate ester of the formula:

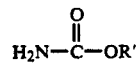

wherein R' is an ester residue, in the presence of a tertiary amine and a tin compound in combination.

6. The method according to claim 5, wherein said tertiary amine is N,N-dimethylbenzylamine, N,N-dimethylaniline, triethylamine, N,N-dimethylcyclohexylamine, N,N,N',N'-tetramethylethylenediamine, N-methylmorpholine, 1,4-diazabicyclo-[2.2.2]octane, 1,8-diazabicyclo-[5.4.0]-7-undecene, pyridine, quinoline or imidazole.

7. The method according to claim 5, wherein said tin compound is stannous chloride, stannous octenate, di-n-butylitin dilaurate, di-n-butyltin oxide, dioctyltin oxide, 1,3-dichlorotetrabutylstannoxane, 2,3-diacetoxytetrabutylstannoxane or dibutyldibutoxytin.

8. The compound according to claim 2, wherein said aliphatic hydrocarbon group is selected from the group consisting of glycidyl, octyl, decyl, lauryl, myristyl, palmityl, stearyl, oleyl and 2-methyloctyl.

9. The compound according to claim 2, wherein said aliphatic hydrocarbon group is lauryl, myristyl, palmityl, stearyl or oleyl.

10. A mixture of compounds of the formula

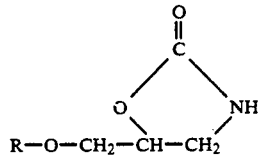

wherein R is a mixture of the aliphatic hydrocarbon groups of 8 to 20 carbon atoms of a naturally occurring oil or fat.

* * * * *